US00PP09648P

United States Patent [19]

Williams

[11] Patent Number: Plant 9,648

[45] Date of Patent: Oct. 1, 1996

[54] SHRUB ROSE PLANT NAMED 'WILVORY'

[76] Inventor: J. Benjamin Williams, 2800 Elnora St., Silver Spring, Md. 20902

[21] Appl. No.: 408,544

[22] Filed: Mar. 22, 1995

[51] Int. Cl.[6] ..... A01H 5/00

[52] U.S. Cl. ..... Plt./1

[58] Field of Search ..... Plt./1, 8.1, 8.2

*Primary Examiner*—Howard J. Locker

[57] ABSTRACT

A new and distinct variety of rose plant of the shrub rose class characterized by its dwarf and compact habit of growth.

1 Drawing Sheet

BACKGROUND OF THE NEW PLANT

The present invention relates to a new and distinct variety of rose plant of the shrub class named 'Wilvory', which was orignated by my crossing as seed parent 'Sea Foam' (U.S. Plant Pat. No. 2,463) with an unnamed seeding (resulting from the cross of 'The Fairy'×'Star Dance') as the pollen parent ('Star Dance' is the subject of U.S. Plant Pat. No. 5,222).

Among the novel characteristics possessed by this new variety which distinguish it from its parents and all other varieties of which I am aware are its:

1. Low growing and vigorously speading compact habit of growth, unlike its seed parent 'Sea Foam';

2. Attractive and unique flower color ranging from bud (Yellow-White Group 158-B) to open bloom (Yellow-White Group 158-D);

3. Substantially continuous and massed blooming habit on shorter than average blooming cycle (three weeks), with the blooms being long-lasting, with petals dropping cleanly;

4. Dark green glossy foliage that is more abundant and more compact than that of either parental cultivar; and 5. Above average disease resistance and excellent winter-hardiness.

Asexual reproduction by budding of the new variety as performed in McFarlin, Calif., and West Grove, Pa., shows that the foregoing and other distinguishing characteristics come true to form and are established and transmitted through succeeding propagations. The plant propagates well from cuttings of new wood as well as from budding.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.). The terminology used in color description herein refers to plate numbers in the aforementioned color chart, e.g., "158-B" is plate 158-B of The Royal Horticultural Society Color Chart.

Description of the New Variety

Flower

A. Bud:
- (1) *Size.*—Small, 1 to 1.5 cm.
- (2) *Form.*—Pointed.
- (3) *Color.*—When sepals divide, bud color is white 158-B.

- (4) *Sepals.*—Slightly longer than bud, sparsely foliated.
- (5) *Peduncle.*—Straight, erect, light green color with a red 47-B overlay.

B. Bloom:
- (1) *Size.*—Small, 2.5–4 cm.
- (2) *Borne.*—Singly with small side buds, and in clusters of 3 to 5 blooms in a spray; mostly erect.
- (3) *Form.*—High-centered to ovoid in form; petals recurl slightly to produce a shingled overlay effect; bloom form is held well, not becoming cupped or flat with age.
- (4) *Petalage.*—Number of petals under normal conditions is 26.
- (5) *Color.*—White 158-D.
- (6) *Color change.*—When first open, color 158-B; fully open bloom changes to 158-D.

C. Petals:
- (1) *Texture.*—Good substance, and recurl well under normal weather conditions without balling or discoloration.
- (2) *Appearance.*—Inside velvety, outside satiny.
- (3) *Form.*—Rounded fan shaped, slight point at apex.
- (4) *Arrangement.*—Imbricated, regularly arranged and slightly cupped.
- (5) *Petaloids in center.*—Few.
- (6) *Persistence.*—Drop off cleanly.
- (7) *Fragrance.*—Slight.
- (8) *Lasting quality.*—On the plant very long (12–15 days).

Reproductive Organs

A. Stamens: Regularly arranged around the pistils.
- (1) *Anthers.*—Color near 10-B.
- (2) *Pollen.*—Color near 10-A.

B. Pistils:
- (1) *Styles.*—Color near 14-B.
- (2) *Stigmas.*—Color 145-C.

C. Hips: None observed.

Plant

A. Form: Dwarf and compact; 12–14 inches high, with a width of 3–4 feet after three years.

B. Growth: Vigorous with uniform branching.

C. Blooming habit: Continuous.

D. Foliage:
- (1) *Size.*—Small.
- (2) *Quantity.*—Abundant, commonly 3–5 leaflets per compound leaf, 5–7 leaves develop on the main canes.
- (3) *Juvenile foliage.*—Closest to 143-C. Mature foliage: Upper-side closest to 143-A. Under-side closest to 143-B.

(4) *Shape.*—Pointed.
(5) *Texture.*—a) Upper side — semi-gloss. b) Under side — matte.
(6) *Edge.*—Serrated.
(7) *Serration.*—Serrulate.
(8) *Leaf stem.*—Color near 143-A.
(9) *Stiples.*—Medium length; smooth.

E. Wood:
(1) *New wood.*—a) Color — 138-A. b) Bark — smooth.
(2) *Old wood.*—a) Color — 143A. b) Bark — smooth.

F. Thorns:
(1) *Quantity.*—Few.
(2) *Form.*—Straight, slightly curved down.
(3) *Length.*—Short (0.5 cm.).

(4) *Color.*—47-B.
(5) *Position.*—Irregular.

G. Prickles:
(1) *Quantity.*—Few.

H. Plant's disease resistance:
(1) *Mildew.*—Above average.
(2) *Blackspot.*—Above average.
(3) *Rust.*—Above average.

I. Winter hardiness: excellent.

I claim:

1. A new and distinct variety of rose plant of the shrub rose class, substantially as herein shown and described.

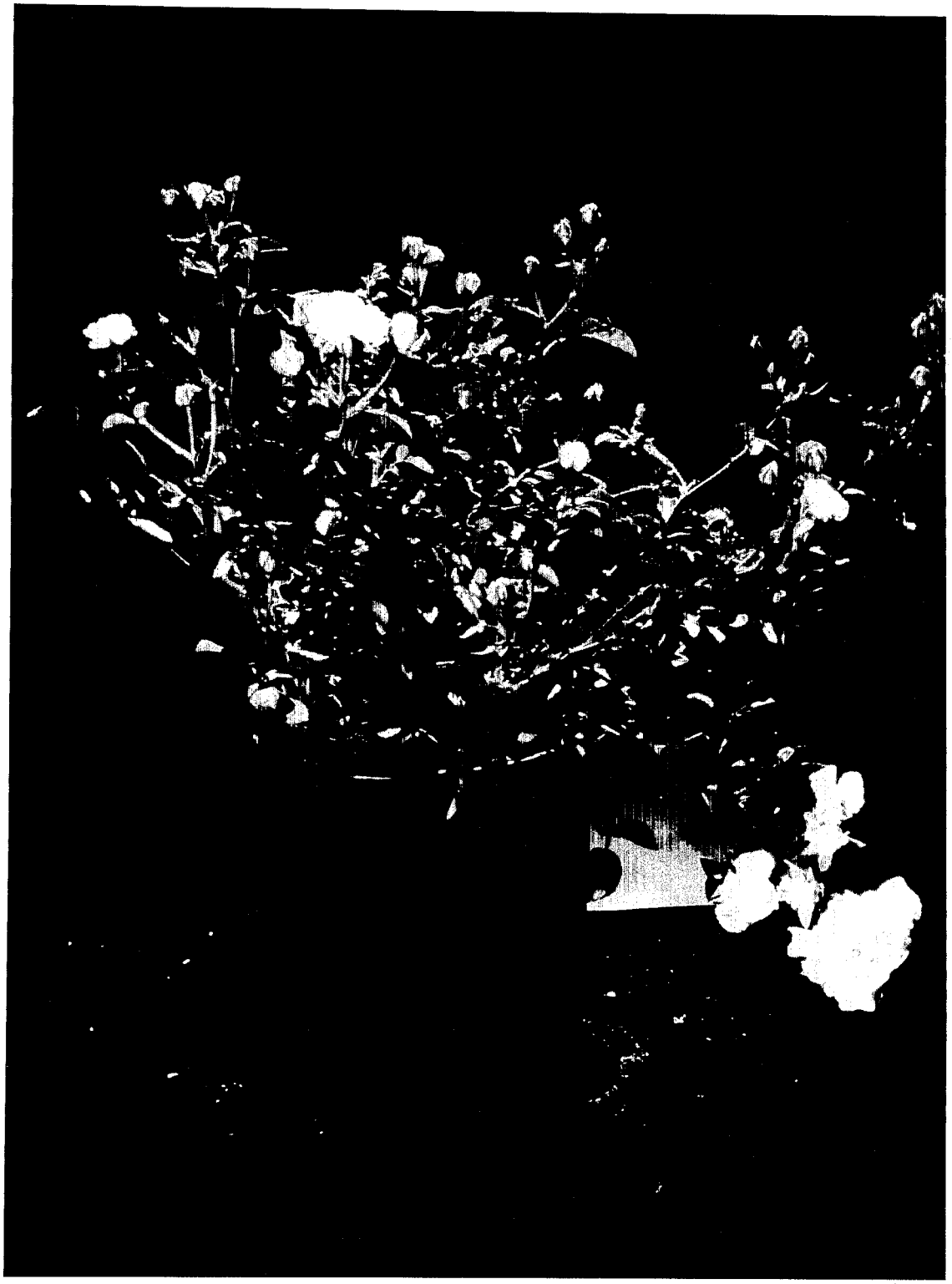

* * * * *